US00PP13772P29

(12) United States Plant Patent
Kievit

(10) Patent No.: US PP13,772 P2
(45) Date of Patent: May 6, 2003

(54) FUCHSIA PLANT NAMED 'KIEFULAP'

(75) Inventor: Christa Kievit, Venhuizen (NL)

(73) Assignee: Kieft Seed Holland, Venhuizen (NL)

( * ) Notice: Subject to any disclaimer, the term of this patent is extended or adjusted under 35 U.S.C. 154(b) by 0 days.

(21) Appl. No.: 10/163,001

(22) Filed: Jun. 5, 2002

(51) Int. Cl.[7] ..... A01H 5/00

(52) U.S. Cl. ..... Plt./300

(58) Field of Search ..... Plt./300

*Primary Examiner*—Kent Bell
(74) *Attorney, Agent, or Firm*—C. A. Whealy

(57) ABSTRACT

A new and distinct cultivar of Fuchsia plant named 'Kiefulap', characterized by its upright and pendulous plant habit; freely branching habit; full and dense plant growth habit; and numerous light red and white-colored flowers.

1 Drawing Sheet

BOTANICAL CLASSIFICATION/CULTIVAR DESIGNATION

*Fuchsia×hybrida* cultivar 'Kiefulap'.

BACKGROUND OF THE INVENTION

The present invention relates to a new and distinct cultivar of Fuchsia plant, botanically known as *Fuchsia×hybrida*, and hereinafter referred to by the name 'Kiefulap'.

The new Fuchsia is a product of a planned breeding program conducted by the Inventor in Venhuizen, The Netherlands. The objective of the breeding program was to create new Fuchsia cultivars with compact plant habit and numerous attractive flower coloration.

The new Fuchsia originated from a cross-pollination made by the Inventor in 1998 of a proprietary selection *Fuchsia×hybrida* identified as code number 6153-1, not patented, as the female, or seed, parent with a proprietary selection *Fuchsia×hybrida* identified as code number 237, not patented, as the male, or pollen, parent. The cultivar Kiefulap was discovered and selected by the Inventor as a flowering plant within the progeny of the stated cross-pollination in a controlled environment in Venhuizen, The Netherlands.

Asexual reproduction of the new Fuchsia by terminal cuttings taken at Venhuizen, The Netherlands, since 1998 has shown that the unique features of this new Fuchsia are stable and reproduced true to type in successive generations.

BRIEF SUMMARY OF THE INVENTION

The cultivar Kiefulap has not been observed under all possible environmental conditions. The phenotype may vary somewhat with variations in environment such as temperature and daylength, without, however, any variance in genotype.

The following traits have been repeatedly observed and are determined to be the unique characteristics of 'Kiefulap'. These characteristics in combination distinguish 'Kiefulap' as a new and distinct Fuchsia cultivar:

1. Upright and pendulous plant habit.

2. Freely branching habit; dense and full plant growth habit.

3. Numerous light red and white-colored flowers.

Plants of the new Fuchsia differ from the parent selections primarily in flower coloration. Plants of the new Fuchsia also differ from plants of the cultivar 'Kiefuzak', U.S. Plant patent application Ser. No. 10/162,985 filed concurrently, primarily in flower coloration.

BRIEF DESCRIPTION OF THE PHOTOGRAPHS

The accompanying colored photographs illustrate the overall appearance of the new Fuchsia, showing the colors as true as it is reasonably possible to obtain in colored reproductions of this type. Colors in the photographs may differ slightly from the color values cited in the detailed botanical description which accurately describe the colors of the new Fuchsia.

The photograph at the top of the sheet comprises a side perspective view of a typical potted plant of 'Kiefulap'.

The photograph at the bottom of the sheet is a close-up view of typical leaves and flowers of 'Kiefulap'.

DETAILED BOTANICAL DESCRIPTION

The aforementioned photographs and following observations and measurements describe plants grown in Lompoc, Calif., under commercial practice during the winter and early spring in a polycarbonate-covered greenhouse with day temperatures about 18 to 24° C., night temperatures about 16 to 18° C., and light levels about 4,000 to 8,000 foot-candles. One cutting was planted per 15-cm container and plants were grown for about 17 weeks. In the following description, color references are made to The Royal Horticultural Society Colour Chart, 1995 Edition, except where general terms of ordinary dictionary significance are used.

Botanical classification: *Fuchsia×hybrida* cultivar Kiefulap.
Parentage:
- *Female or seed parent.*—Proprietary selection of *Fuchsia×hybrida* identified as code number 6153-1, not patented.
- *Male, or pollen, parent.*—Proprietary selection of *Fuchsia×hybrida* identified as code number 237, not patented.

Propagation:
- *Type cutting.*—Terminal cuttings.
- *Time to initiate roots, summer and winter.*—About 14 days at 21° C.

*Time to produce a rooted cutting.*—Summer: About 28 days at 21° C. Winter: About 32 days at 21° C.

*Root description.*—Fine, fibrous and freely-branching.

Plant description:

*Form.*—Upright and pendulous plant habit, relatively compact and freely branching habit; dense and full plants. Freely flowering. Appropriate for 10 to 15-cm containers. Moderately vigorous.

*Plant height at flowering.*—About 24 cm.

*Plant diameter at flowering.*—About 32 cm.

*Branching habit.*—Freely branching; typically 22 lateral branches develop per plant. Pinching (removal of terminal apex) enhances lateral branch development.

*Lateral branch description.*—Length: About 22 cm. Diameter: About 4 mm. Internode length: About 3.25 cm. Aspect: Initially upright to pendulous with flower development. Strength: Strong. Texture: Pubescent. Color: 144B to 144C.

*Foliage description.*—Arrangement: Simple, opposite. Length: About 4.7 cm. Width: About 1.8 cm. Shape: Elliptic. Apex: Narrowly acute. Base: Attenuate. Margin: Irregularly serrulate. Texture, upper and lower surfaces: Smooth, glabrous. Venation pattern: Pinnate. Petiole length: About 2.4 cm. Petiole diameter: About 2 mm. Petiole texture, upper and lower surfaces: Smooth, glabrous. Color: Young leaves, upper surface: 138A. Young leaves, lower surface: 138B. Fully expanded leaves, upper surface: 147A. Fully expanded leaves, lower surface: 147B. Venation, upper surface: 147B. Venation, lower surface: 147D. Petiole, upper and lower surfaces: 145A.

Flower description:

*Flower type and habit.*—Single bi-colored axillary flowers. Freely flowering; potentially two flowers per leaf axil; about eight open flowers per lateral branch. Flowers not persistent. Flowers not fragrant.

*Natural flowering season.*—April through October in northern Europe; flowering recurrent.

*Flower longevity.*—Flowers last about five days on the plant.

*Flower orientation.*—Initially upright, then pendulous.

*Flower diameter.*—About 5 cm.

*Flower height.*—About 5.2 cm.

*Flower buds.*—Shape: Ovoid. Length: About 3 cm. Width: About 8 mm. Color: 52A.

*Petals.*—Quantity: Four; imbricate. Length: About 1.2 cm. Width: About 1.2 cm. Shape: Fan-shaped to roughly cordate. Apex: Emarginate. Margin: Entire, undulate. Texture, upper and lower surfaces: Glabrous, smooth and satiny. Color: When opening, upper surface: 155C; towards base, 55A. When opening, lower surface: 155C; towards base, 55B. Fully opened, upper surface: 155C; towards base, 54C. Fully opened, lower surface: 155C; towards base, 54C to 54D.

*Sepals.*—Quantity: Four; fused at base. Length: About 3 cm. Width: About 6 mm. Aspect: Flat; recurved. Shape: Narrowly elliptic. Apex: Acute. Margin: Entire. Texture, upper and lower surfaces: Glabrous, smooth. Color: When opening and fully opened, upper surface: 52A. When opening and fully opened, lower surface: 52A.

*Peduncles.*—Length: About 1.5 cm. Diameter: About 1.5 mm. Aspect: Arching to horizontal. Strength: Moderately strong. Texture: Smooth, glabrous. Color: 144C.

*Reproductive organs.*—Stamens: Stamen number: Eight per flower. Anther length: About 2 mm. Anther diameter: About 2 mm. Anther shape: Oblong. Anther color: 50A. Pollen amount: Scarce. Pollen color: 155B. Pistils: Pistil number: One per flower. Pistil length: About 5 cm. Style length: About 4.3 cm. Style color: 55A. Stigma shape: Rounded oblong. Stigma color: 55A. Ovary color: 144A.

*Seed/fruit.*—Seed and fruit production has not been observed.

Disease/pest resistance: Plants of the new Fuchsia have not been observed to be resistant to pathogens and pests common to Fuchsias.

Temperature tolerance: Plants of the new Fuchsia have been observed to tolerate low temperatures of 10° C. and high temperatures of 30° C.

Garden performance: Plants of the new Fuchsia have been observed to perform well in the garden and are tolerant to rain and wind.

It is claimed:

1. A new and distinct cultivar of Fuchsia plant named 'Kiefulap', as illustrated and described.

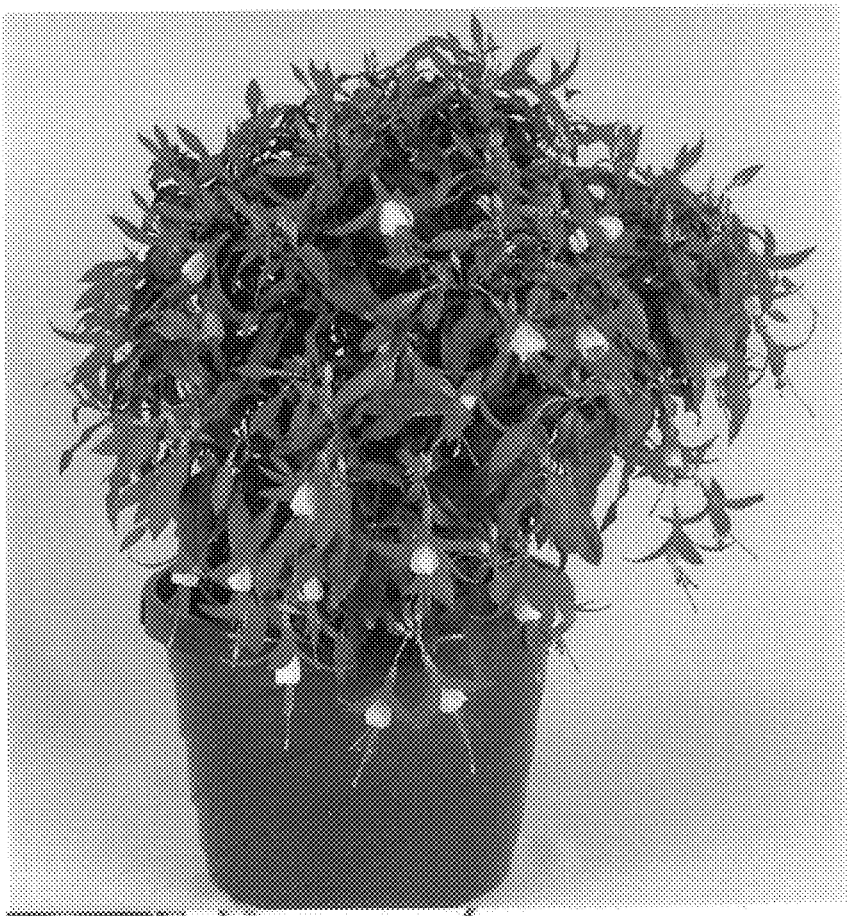
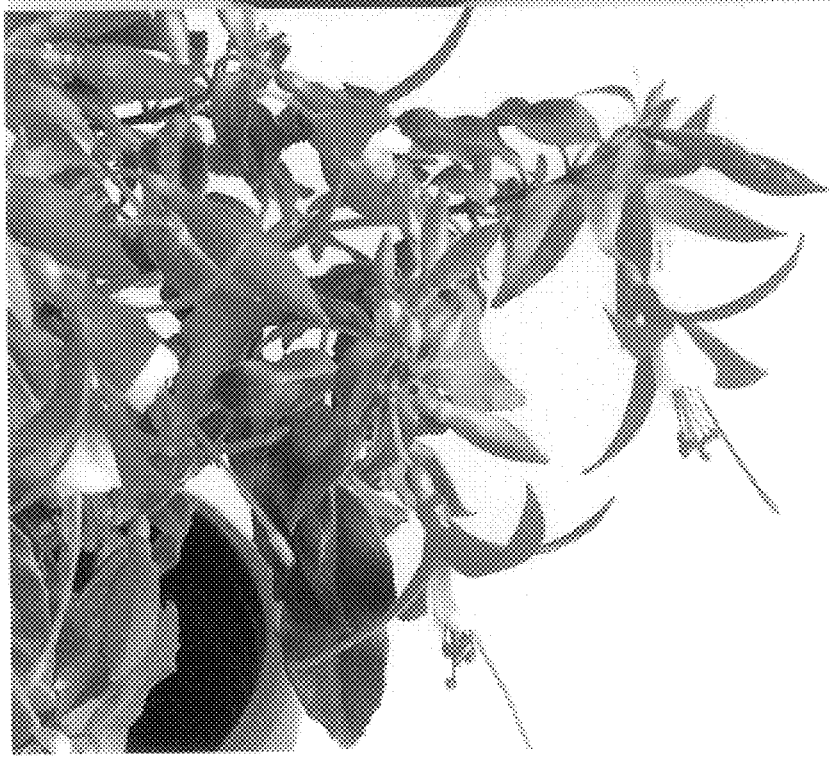

* * * * *